United States Patent
Oostman, Jr. et al.

(10) Patent No.: US 10,076,352 B2
(45) Date of Patent: Sep. 18, 2018

(54) IMPLANTATION NEEDLE

(71) Applicant: Restoration Robotics, Inc., San Jose, CA (US)

(72) Inventors: Clifford A. Oostman, Jr., Hansville, WA (US); Steven E. Jakubowski, Mountain View, CA (US)

(73) Assignee: RESTORATION ROBOTICS, Inc., San Jose, CA (US)

( * ) Notice: Subject to any disclaimer, the term of this patent is extended or adjusted under 35 U.S.C. 154(b) by 78 days.

(21) Appl. No.: 15/142,138

(22) Filed: Apr. 29, 2016

(65) Prior Publication Data
US 2016/0345999 A1    Dec. 1, 2016

Related U.S. Application Data

(60) Provisional application No. 62/168,222, filed on May 29, 2015.

(51) Int. Cl.
*A61B 17/34* (2006.01)
*A61B 17/3205* (2006.01)
*A61B 17/00* (2006.01)

(52) U.S. Cl.
CPC .... *A61B 17/32053* (2013.01); *A61B 17/3468* (2013.01); *A61B 2017/00752* (2013.01)

(58) Field of Classification Search
CPC . A61B 17/34; A61B 17/3417; A61B 17/3468; A61B 17/32053; A61B 17/06; A61B 17/06066; A61B 2017/00752; A61B 2017/3454; A61B 2017/06071; A61B 2017/061

USPC .................. 606/185, 187, 222, 223
See application file for complete search history.

(56) References Cited

U.S. PATENT DOCUMENTS

| | | | |
|---|---|---|---|
| 1,433,340 | A | 10/1922 | Clark |
| 2,560,162 | A | 7/1951 | Ferguson |
| 3,071,135 | A | 1/1963 | Baldwin et al. |
| 3,308,822 | A | 3/1967 | De Luca |
| 3,605,721 | A | 9/1971 | Hallac |
| 3,867,942 | A | 2/1975 | Bellantoni et al. |
| 3,998,230 | A | 12/1976 | Miller |

(Continued)

FOREIGN PATENT DOCUMENTS

| | | |
|---|---|---|
| EP | 0966920 A2 | 12/1999 |
| EP | 1293167 A2 | 3/2003 |

(Continued)

OTHER PUBLICATIONS

Inaba, M. et al.; "Androgenetic Alopecia, Modem Concepts of Pathogenesis and Treatment", 29. Operative Treatment for Androgenetic Alopecia, Springer, 1996, pp. 238-244; 309 (9 pages).

(Continued)

*Primary Examiner* — Melanie Tyson (57) ABSTRACT

A non-coring hair implantation needle is provided which provides for a smaller opening than a conventional hypodermic needle, and includes a bevel of shorter length. The needles are configured to provide a non-cutting feature, and aid in placement and retention of an implanted hair graft when the needle is withdrawn from the body surface. Furthermore, methods of fabricating needles includes bevels of shorter length and non-cutting features are disclosed.

14 Claims, 5 Drawing Sheets

(56) References Cited

U.S. PATENT DOCUMENTS

| | | |
|---|---|---|
| 4,128,351 A | 12/1978 | Kurtz et al. |
| 4,160,453 A | 7/1979 | Miller |
| 4,383,530 A | 5/1983 | Bruno |
| 4,461,305 A | 7/1984 | Cibley |
| 4,476,864 A | 10/1984 | Tezel |
| 4,479,291 A | 10/1984 | Yamada |
| 4,490,139 A | 12/1984 | Huizenga et al. |
| 4,640,296 A | 2/1987 | Schnepp-Pesch et al. |
| 4,708,147 A | 11/1987 | Haaga |
| 4,716,901 A | 1/1988 | Jackson et al. |
| 4,785,826 A | 11/1988 | Ward |
| 5,036,860 A | 8/1991 | Leigh et al. |
| 5,183,053 A | 2/1993 | Yeh et al. |
| 5,341,816 A | 8/1994 | Allen |
| 5,423,330 A | 6/1995 | Lee |
| 5,439,475 A | 8/1995 | Bennett |
| 5,480,388 A | 1/1996 | Ladini et al. |
| 5,562,613 A | 10/1996 | Kaldany |
| 5,573,008 A | 10/1996 | Robinson et al. |
| 5,578,054 A | 11/1996 | Arnold |
| 5,584,841 A | 12/1996 | Rassman |
| 5,651,781 A | 7/1997 | Grace |
| 5,658,272 A | 8/1997 | Hasson |
| 5,693,064 A | 12/1997 | Arnold |
| 5,733,266 A | 3/1998 | Gravlee, Jr. |
| 5,752,942 A | 5/1998 | Doyle et al. |
| 5,782,851 A | 7/1998 | Rassman |
| 5,782,853 A | 7/1998 | Zeevi et al. |
| 5,788,651 A | 8/1998 | Weilandt |
| 5,792,163 A | 8/1998 | Hitzig |
| 5,817,120 A | 10/1998 | Rassman |
| 5,827,199 A | 10/1998 | Alexander |
| 5,827,297 A | 10/1998 | Boudjema |
| 5,858,019 A | 1/1999 | Ashraf |
| 5,885,226 A | 3/1999 | Rubinstein et al. |
| 5,893,853 A | 4/1999 | Arnold |
| 5,895,403 A | 4/1999 | Collinsworth |
| 5,910,121 A | 6/1999 | Paolo et al. |
| 5,961,529 A | 10/1999 | Arnold |
| 5,981,529 A | 11/1999 | Baker et al. |
| 6,015,391 A | 1/2000 | Rishton et al. |
| 6,059,807 A | 5/2000 | Boudjema |
| 6,080,175 A | 6/2000 | Hogendijk |
| 6,086,543 A | 7/2000 | Anderson et al. |
| 6,110,189 A | 8/2000 | Markman |
| 6,120,521 A | 9/2000 | Casparian |
| 6,142,955 A | 11/2000 | Farascioni et al. |
| 6,273,861 B1 | 8/2001 | Bates et al. |
| 6,315,737 B1 | 11/2001 | Skinner |
| 6,395,002 B1 | 5/2002 | Ellman et al. |
| 6,416,484 B1 | 7/2002 | Miller et al. |
| 6,461,369 B1 | 10/2002 | Kim |
| 6,464,711 B1 | 10/2002 | Emans et al. |
| 6,471,709 B1 | 10/2002 | Fawzi et al. |
| 6,488,636 B2 | 12/2002 | Bryan et al. |
| 6,554,779 B2 | 4/2003 | Viola et al. |
| 6,572,625 B1 | 6/2003 | Rassman |
| 6,585,746 B2 | 7/2003 | Gildenberg |
| 6,702,790 B1 | 3/2004 | Ross et al. |
| 6,775,879 B2 | 8/2004 | Bibeault et al. |
| 6,939,318 B2 | 9/2005 | Stenzel |
| 7,070,583 B1 | 7/2006 | Higuchi et al. |
| 7,172,604 B2 | 2/2007 | Cole |
| 7,201,722 B2 | 4/2007 | Krueger |
| 7,261,721 B2 | 8/2007 | Feller |
| 7,468,055 B2 | 12/2008 | Prais et al. |
| 8,273,062 B2 | 9/2012 | Villette |
| 2001/0034534 A1 | 10/2001 | Transue |
| 2002/0103500 A1 | 8/2002 | Gildenberg |
| 2002/0151821 A1 | 10/2002 | Castellacci |
| 2003/0097079 A1 | 5/2003 | Garcia |
| 2003/0097144 A1 | 5/2003 | Lee |
| 2004/0092924 A1 | 5/2004 | Vasa |
| 2004/0116942 A1 | 6/2004 | Feller |
| 2004/0220589 A1 | 11/2004 | Feller |
| 2005/0004592 A1 | 1/2005 | Criscuolo |
| 2005/0096687 A1 | 5/2005 | Rassman et al. |
| 2005/0131313 A1 | 6/2005 | Mikluka et al. |
| 2005/0187573 A1 | 8/2005 | Rassman et al. |
| 2005/0245952 A1 | 11/2005 | Feller |
| 2005/0267506 A1 | 12/2005 | Harris |
| 2006/0161179 A1 | 7/2006 | Kachenmeister |
| 2006/0173476 A1 | 8/2006 | Bradica et al. |
| 2006/0178678 A1 | 8/2006 | Cole |
| 2007/0078466 A1 | 4/2007 | Bodduluri et al. |
| 2007/0078473 A1 | 4/2007 | Bodduluri et al. |
| 2007/0106307 A1 | 5/2007 | Bodduluri et al. |
| 2007/0123800 A1 | 5/2007 | Nishtala et al. |
| 2007/0123935 A1* | 5/2007 | Myers ............... A61B 17/3421 606/222 |
| 2007/0142743 A1 | 6/2007 | Provencher et al. |
| 2007/0149985 A1 | 6/2007 | Cole |
| 2007/0156164 A1 | 7/2007 | Cole |
| 2007/0213741 A1 | 9/2007 | Cole |
| 2008/0033455 A1 | 2/2008 | Rassman et al. |
| 2008/0154150 A1 | 6/2008 | Goldenberg |
| 2008/0154296 A1 | 6/2008 | Taylor et al. |
| 2008/0234602 A1 | 9/2008 | Oostman et al. |
| 2008/0234699 A1 | 9/2008 | Oostman et al. |
| 2009/0227895 A1 | 9/2009 | Goldenberg |
| 2009/0240261 A1 | 9/2009 | Drews et al. |
| 2010/0082042 A1 | 4/2010 | Drews |
| 2011/0160746 A1 | 6/2011 | Umar |
| 2012/0265216 A1 | 10/2012 | Cole |
| 2014/0031839 A1 | 1/2014 | Umar et al. |
| 2014/0288579 A1 | 9/2014 | Umar |
| 2015/0018844 A1 | 1/2015 | Harris |
| 2015/0038985 A1 | 2/2015 | Cole |
| 2015/0223840 A1 | 8/2015 | Wesley et al. |
| 2015/0250493 A1 | 9/2015 | Umar |
| 2015/0250494 A1 | 9/2015 | Umar |
| 2015/0272611 A1 | 10/2015 | Harris |
| 2015/0305472 A1 | 10/2015 | Umar et al. |
| 2015/0305767 A1 | 10/2015 | Cole |
| 2016/0235441 A1 | 8/2016 | Parkin |
| 2016/0249948 A1 | 9/2016 | Umar |
| 2016/0317227 A1 | 11/2016 | Chandler et al. |
| 2017/0095237 A1 | 4/2017 | Wesley et al. |

FOREIGN PATENT DOCUMENTS

| | | |
|---|---|---|
| GB | 2006017 A | 5/1979 |
| WO | 9706749 A1 | 2/1997 |
| WO | 0207602 A2 | 1/2002 |
| WO | 2005109799 A2 | 11/2005 |
| WO | 2006081556 A2 | 8/2006 |
| WO | 2007021904 A2 | 2/2007 |
| WO | 2008027829 A2 | 3/2008 |
| WO | 2009017445 A1 | 2/2009 |

OTHER PUBLICATIONS

Robert Bernstein, MD, et al.; New Instrumentation for Three-Stop Follicular Unit Extraction, Hair Transplant forum International, vol. 16, No. 1, Jan./Feb. 2006.

Harris, James A., "New Methodology and Instrumentation for Follicular Unit Extraction: Lower Follicle Transection Rates and Expanded Patient Candidacy," Department of Otolaryngolgy/Headand Neck Surgery, Univ. of Colorado Health Sciences Center, Denver CO; 2006 by the American Society of Dermatologic Surgery, Inc., BC Decker, vol. 32.

"New Instrument for Hair Transplant: Multichannel Hair Transplanter"; The American Society for Dermatologic Surgery, Inc.; BC Decker Inc., 1 pg.; 2005.

* cited by examiner

IMPLANTATION NEEDLE

This application claims priority under 35 U.S.C. 119(e) to U.S. Provisional Application No. 62/168,222 filed May 29, 2015, entitled "Implantation Needle".

TECHNICAL FIELD

This application relates generally to implantation tools. In particular, this application relates to implantation tools for implanting hair follicular units or hair grafts, in a body surface.

BACKGROUND

Conventional hypodermic needles are optimized for injections and are non-coring needles, typically long pointed steel tubes that are pushed through the skin to provide subcutaneous injections. They are typically used to deliver fluids, medicine, or to take samples of blood or other fluids. Subcutaneous injections into the fat layer between the skin and muscle are typically given at a depth of greater than 3.5 mm. Needles utilized to withdraw blood are typically inserted to a depth of between 7-10 mm below the skin surface. The geometry of such needles attempts to guarantee that the needle will penetrate the body surface by making the tip of the needle pointed, and designing the remainder of the opening of the needle such that "coring" is minimized. Coring is the result achieved when a portion of tissue material through which that needle has penetrated obstructs the lumen of the needle, proximal to the pointed tip. In addition, the geometry of such needles typically aims to reduce the pain and discomfort experienced by patients who are undergoing such procedures. With the purposes and applications for which typical hypodermic needles are used, they are generally adequate.

The implantation of follicular units or hair grafts poses a unique problem, requiring the insertion of a follicular unit or hair graft containing naturally occurring aggregates of 1 to 4 hair follicles, into a body surface at a depth which is typically no greater than 4-5 mm. Usually, in known hair implantation procedures using hand-held tools, incisions for implantation sites may be made by a blade or by a conventional non-coring needle or cannula, and then the previously harvested hair grafts are placed manually by the physician or technician in such sites with the use of forceps. Therefore, to improve the efficiency of the implantation procedure, there is a need for instruments and methodologies that allow for the effective implantation of hair grafts through the needle or cannula without the use of the forceps. Such implantation of follicular units using a needle or cannula presents issues which are not encountered or considered when using a hypodermic needle in a conventional manner, such as for example, requiring that the implanted hair graft and those around it remain implanted when the needle is withdrawn, and additionally imposing that the integrity of the follicular unit or hair graft be maintained, a problem which a typical hypodermic needle does not address.

SUMMARY

The present disclosure provides new improved designs for implantation needles and the methods of their manufacture. According to one aspect of the disclosure, an implantation needle is provided with a specially configured relief portion. While such a needle is especially useful for hair implantation, it may be used in other applications. The needle comprises an elongated body having a longitudinal axis, a lumen sized to receive a biological unit or tissue (such as a follicular unit) and a distal end with a distal tip configured to penetrate a body surface; the distal end comprises a beveled portion extending from the distal tip, for example, oblique to the central longitudinal axis of the elongated body and a relief portion extending from the beveled portion in a proximal direction. The relief portion may comprise a narrow cut-out in a wall of the elongated body, wherein the cut-out is substantially parallel to the longitudinal axis. According to certain embodiments, the beveled portion and the relief portion are configured and sized relative to each other such that to prevent coring and provide a non-coring needle. According to some embodiments, the relief portion may have a length of approximately 40% to 100% of the length of the beveled portion. The beveled portion and the relief portion are sized relative to each other in a manner to keep the needle insertion forces low as the needle is being inserted beyond the distal tip. The beveled portion and the relief portion together may form an oblique opening at the distal end of the needle, and the beveled portion and the relief portion may be sized relative to each other such that the length of the oblique opening is less than the length of the biological unit or tissue to be implanted. With reference to hair grafts, the length of the oblique opening may be, for example, 1.0 mm to 2.5 mm shorter than the length of the hair graft. In some implementations, it may be also desirable that the length of the opening be less than a depth of an incision to be formed by the implantation needle. Further, according to some embodiments, the length of the opening formed by the beveled and the relief portions may be in a range of 3 mm to 5 mm, for example 4 mm or less.

In some embodiments, the distal tip may comprise a blade-style cutting edge, which may comprise at least three cutting segments. The blade-style cutting edge may comprise an inclined surface, which may taper toward an outer wall of the elongated body. In certain embodiments the relief portion comprises a proximal edge having a non-cutting edge. The width of the relief portion may be up to 90% of the outside diameter of the lumen, for example, between 50% and 80% of an outside diameter of the lumen.

According to some embodiments, a hair implantation needle is provided which comprises an elongated body having a longitudinal axis and a lumen sized to receive a follicular unit; and a distal end with a distal tip configured to penetrate a body surface. The distal end is non-coring and comprises a beveled portion extending from the distal tip oblique to the longitudinal axis of the elongated body; and a relief portion extending from the beveled portion in a proximal direction. The relief portion comprises a narrow cut-out in a wall of the elongated body substantially parallel to the longitudinal axis, wherein a length of the relief portion is approximately 40% to 100% of the length of the beveled portion. For example, for hair implantation needles of 18 to 21 gauges, the combined length of an opening formed by the beveled portion and the relief portion may be in a range of 3 mm to 4 mm.

According to yet another aspect, an implantation needle is provided with a specially designed distal tip and a plurality of cutting segments extending from the distal tip. According to this aspect, the needle comprises an elongated body having a wall with an outer and inner wall surface, a longitudinal axis, and a lumen formed by the inner wall surface and sized to receive a follicular unit. The needle further comprises a distal end having a distal tip configured to penetrate a body surface. In certain embodiments, the distal end of the needle may comprise a primary cutting segment, at least two additional cutting segments with blade-style leading cutting edges and a slanted or oblique external cutting surface extending in a proximal direction from each of the at least two additional cutting segments; wherein the slanted external cutting surface has an external inclined plane slanted towards the inner wall surface of the lumen along its length. In some embodiments, the distal end comprises a beveled portion and the slanted external cutting surface is formed within the beveled portion. In other embodiments, the implantation needle further comprises a relief portion comprising a narrow cut-out in the wall of the elongated body that may be substantially parallel to the longitudinal axis. In certain embodiments, the relief portion may extend from the beveled portion in a proximal direction.

According to a further aspect of the disclosure, a hair implantation needle is provided, the needle comprising an elongated body having a longitudinal axis and a lumen sized to receive a follicular unit; a distal end with a distal tip configured to penetrate a body surface. The distal end is non-coring and comprises a beveled portion extending from the distal tip oblique to the longitudinal axis of the elongated body and a relief portion extending from the beveled portion in a proximal direction. The relief portion comprises a narrow cut-out in a wall of the elongated body substantially parallel to the longitudinal axis. The distal tip comprises a plurality of cutting segments, for example, at least two or at least three cutting segments, with blade-style leading cutting edges. The beveled portion comprises a slanted external cutting surface extending in a proximal direction from at least one of the at least two or three cutting segments. In some embodiments the slanted external cutting surface comprises an inclined plane slanted towards an inner wall surface of the lumen of the elongated body. The inclined plane is not substantially parallel to the axis of the elongated body.

According to another aspect of the disclosure, methods are provided for fabricating hair implantation needles in accordance with the present disclosure. These fabrication methods may comprise utilization of conventional equipment, without any significant increase in manufacturing costs.

Needles and methods of the present disclosure may be implemented for use with manual, partially automated and fully automated, including robotic, systems and procedures, for example, for implantation of biological units, including follicular units. Other and further objects and advantages of the disclosure will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to be limiting. Features and advantages of the embodiments described herein will become appreciated as the same become better understood with reference to the specification, claims, and appended drawings wherein:

DETAILED DESCRIPTION OF SPECIFIC EMBODIMENTS

In the following Detailed Description, reference is made to the accompanying drawings, in which are shown by way of illustration specific embodiments in which the invention may be practiced. In this regard, directional terms such as "top," "bottom,", "upper", "lower", "front," "back," "distal," "proximal," etc., are used with reference to the orientation of the Figure(s) being described. Because components or embodiments of the present disclosure can be positioned in a number of different orientations, the directional terminology is used for purposes of illustration and is in no way limiting. It is to be understood that other embodiments may be utilized and structural or logical changes may be made without departing from the scope of the present disclosure. The following Detailed Description, therefore, is not to be taken in a limiting sense, and the scope of the present disclosure is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input.

The term "tool," as used herein refers to any number of tools or end effectors that are capable of performing an action, procedure or operation in various cosmetic, medical and other procedures or applications. For example, the tool may be a needle or cannula adapted for use in various dermatological applications, tissue grafting, injection of fat cells, for example, into a subcutaneous fat layer for facial or body "lipo-contouring", collagen implantation, injection of hyaluronic acid products and/or muscle inhibitors (e.g., Botox®), procedures for facial or body rejuvenation or reconstruction, for example, involving making a number of injections of minute amounts of substances into targeted intradermal and subcutaneous tissues, or the administration of medication. A "tool" or "implanting tool" as used in reference to a hair transplantation procedure refers to any number of tools or end effectors that are capable of making incisions/implanting/inserting follicular units ("FUs") into a body surface. Such tools may have many different forms and configurations. In some embodiments, the tool comprises a hollow tubular shaft. The distal end of the tools (for example, punches, cannulas, needles), are typically sharpened, to pierce or cut the tissue. Implanting tools, for example, hair implantation or site making needles, may also be sharpened so as to perform puncture and delivery of the FU in one operation.

The terms "operatively connected," "coupled," "mounted" or "attached" as used herein, means directly or indirectly connected, coupled, mounted or attached through one or more intervening components. Embodiments of the methods of the present disclosure may be implemented using computer software, firmware or hardware. Various programming languages and operating systems may be used to implement the present disclosure.

The present disclosure is especially applicable to the needles or cannulas for use in hair implantation, and therefore, the following disclosure, for convenience and as an example only, will be provided in reference to such needles. It should be apparent, however, that although the various examples and embodiments described will refer to the needles for implantation of the follicular units (naturally occurring aggregates of 1 to 4 hair follicles) or hair grafts, the general understanding of the various concepts discussed can be applied more broadly to needles for use in other appropriate applications. For example, various applications and procedures where it is beneficial to make an incision without coring tissue and keeping the needle insertion forces low not only initially but also as the needle or cannula continues to be inserted beyond the distal tip, may benefit from the instruments and methods of the present disclosure. The needles, punches or cannulas described herein may be utilized, for example, in medication delivery, various dermatological procedures or treatment of various dermatological conditions. Similarly, the present disclosure may be applied, for example, to objects other than follicular units or hair grafts. The present disclosure is particularly beneficial in semi-automated, automated, or robotic procedures, such as robotic hair transplantation procedures.

Figure 1:
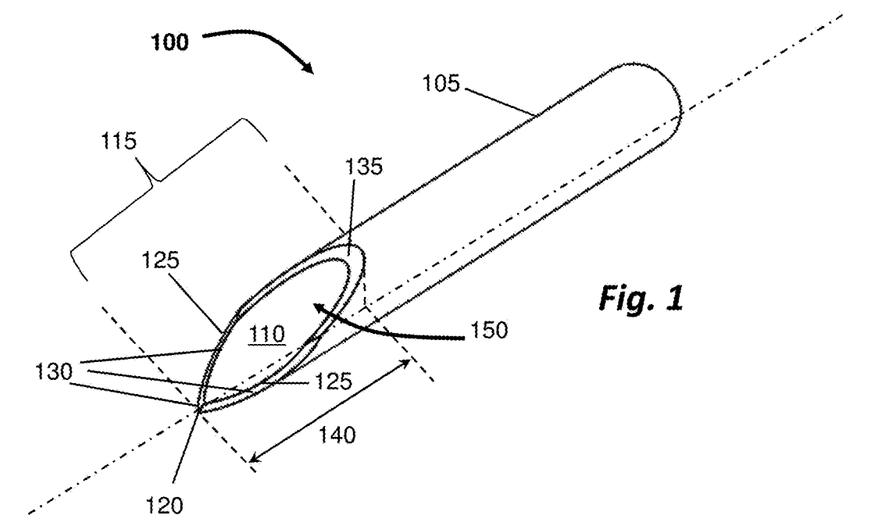
FIG. 1 is a schematic perspective view of a conventional hypodermic needle.

Conventional needles or cannulas that are currently used to make incisions (or sites) in manual or partially automated hair implantation procedures typically have a very large bevel length and very narrow points. These needles, however, are optimized for injections, but not for site-making. FIG. 1 shows an example of such typical hypodermic needle 100, comprising a long elongated body 105 forming a substantially hollow lumen 110 therein, the elongated body formed of conventional materials such as stainless steel. The distal end 115 of the hypodermic needle 100 comprises a slanted or oblique opening 150 having a length dictated in part by the gauge of the needle, for example, for a 19 gauge needle, the length of the opening is usually in the range of 4-5 mm with 4.74 mm being one example of a typical length. The opening 150 forms a narrow pointed distal tip 120 for penetrating a body surface. One or more beveled surface or surfaces 125 are formed about a periphery of the slanted opening 150 (extending from the inner wall of the elongated body to the outer wall of the elongated body 105). Such needles 100 are typically manufactured using a combination of cutting and grinding procedures. The first cut at an angle to the axis of the elongated body forms a cylinder with a planar angle cut tip. The distal portion of the planar angle cut tip is then processed, typically by grinding, to form the beveled surfaces 125. The combination of procedures forms a cutting edge 130 comprising the sharp distal tip 120 and the adjacent beveled surfaces 125. The cutting edge 130 and the heel surface or heel 135 together aid in creation of an arcuate shaped incision ("smiley face") in the body surface as the needle penetrates the body surface.

In use, the distal tip 120 of the hypodermic needle 100 progressively penetrates the body surface, with the insertion forces required to penetrate the tissue below the body surface increasing as the needle is inserted beyond the pointed distal tip 120. Initially, the surface of the body surface is cut only with the very tip of the needle. As penetration of the needle continues, the portion of the needle beyond the distal tip 120 tears the surrounding tissue as it is stretched around the needle as it enters the through the incision. The resulting surface wound resembles a semicircular or arcuate cut.

Implantation of follicular units or hair grafts poses a unique problem, requiring the insertion of a follicular unit or hair graft into the body surface without substantially damaging the integrity thereof, a problem which typical use of a hypodermic needle or cannula, such as the one shown in FIG. 1, does not address. It has been discovered by applicant that this is at least partially due to the fact that the length 140 of the opening 150 of such conventional needle is too long relative to the typical length of a hair graft (as described in reference to FIG. 3). During implantation of a hair graft, the subsurface of the skin makes contact with the needle bevel, and the hair graft must therefore push the flesh it comes into contact with sideways while it is being pushed through the cannula. As a substantial portion of the hair graft is exposed in the opening of the bevel, a significant portion of the hair graft may therefore potentially be damaged. Minimizing the length of the beveled portion of the needle should therefore result in a corresponding reduction to the side force on the graft as it is being pushed out of the implantation needle.

Typically, a 19 gauge hypodermic needle has an opening with a bevel length of between 4 and 5 mm. In terms of follicular unit extractions, most procedures are performed using 16 to 21 gauge needles, typically with needles of gauge 18-21, with the higher gauge number representing a smaller diameter needle, and the bevel length of each gauge of needle varying according to its outer and inner wall diameters. It has been found by applicant that ideally, for hair transplantation, the bevel on an implant needle should be on the order of 2-3 mm, and further on the order of 2.5-3 mm, to protect a hair graft while it is being pushed into the scalp, for example, by an obturator or by using a pressure differential.

Figure 2A:
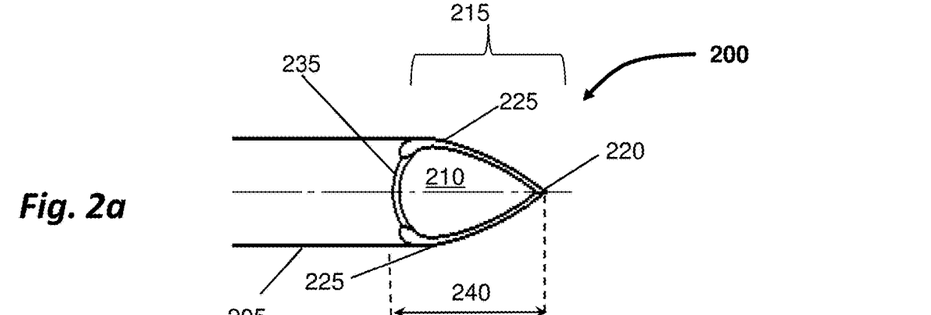
FIGS. 2a and 2b illustrate a schematic representation of the top and side view of an example of a conventional needle with a minimized length of the needle bevel.
Figure 2B:
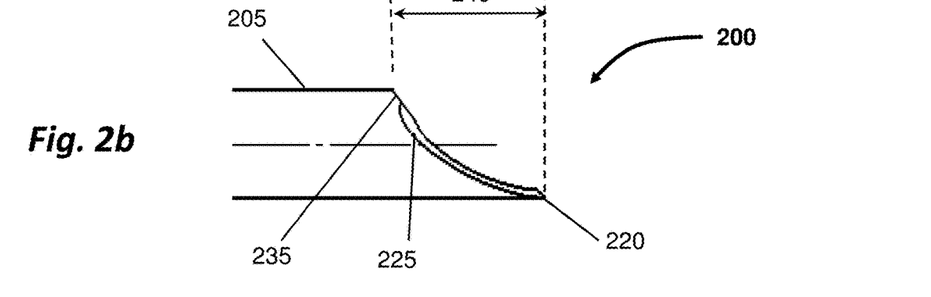

FIGS. 2a and 2b illustrate such a shorter bevel needle and explain the new issues that arise when the conventional needle is modified simply by reducing the length of the bevel. FIG. 2a shows the needle 200 disposed horizontally and as viewed from above. FIG. 2b is a side view of the needle of FIG. 2a. The implantation needle 200 comprises an elongated body 205 forming a lumen 210 therein, the lumen 210 configured to accommodate an individual follicular unit or hair graft therein. The distal end 215 of the implantation needle 200 comprises a pointed distal tip 220 for penetrating a body surface. Beveled surfaces 225 aid in creating the sharp pointed distal tip 220. An opening at the distal end also has a heel portion 235. The length of the bevel 240 (that may be measured as the distance along a central longitudinal axis of the elongated body 205 that the beveled surfaces 225 project onto up to the distal tip 220) is substantially shorter than in the conventional needle of FIG. 1, for example, 2.4 mm. This reduced length can be achieved, for example, by varying the angle of the beveled surfaces 225. This configuration results in the reduced forces and protects a substantial portion of a follicular unit from being compressed as it experiences a side-ways force from the surrounding tissue as the follicular unit is urged out the distal end of the implantation needle by the obturator or other such urging means and into the body surface. However, it was discovered that simply minimizing the length of the needle bevel as shown in the example of FIGS. 2a and 2b results in the heel portion 235 acting as a secondary cutting edge creating a coring cut in the tissue and, as a result, turning the shorter bevel needle into a "coring" needle. In other words, instead of creating a semi-circular incision, the needle of FIGS. 2a and 2b cores/removes tissue creating a circular hole. As explained earlier, coring results in a portion of the tissue material being removed and entering the lumen of the needle, which is undesirable in certain applications, such as for example, creating sites for implanting hair grafts.

Figures 3, 4A:
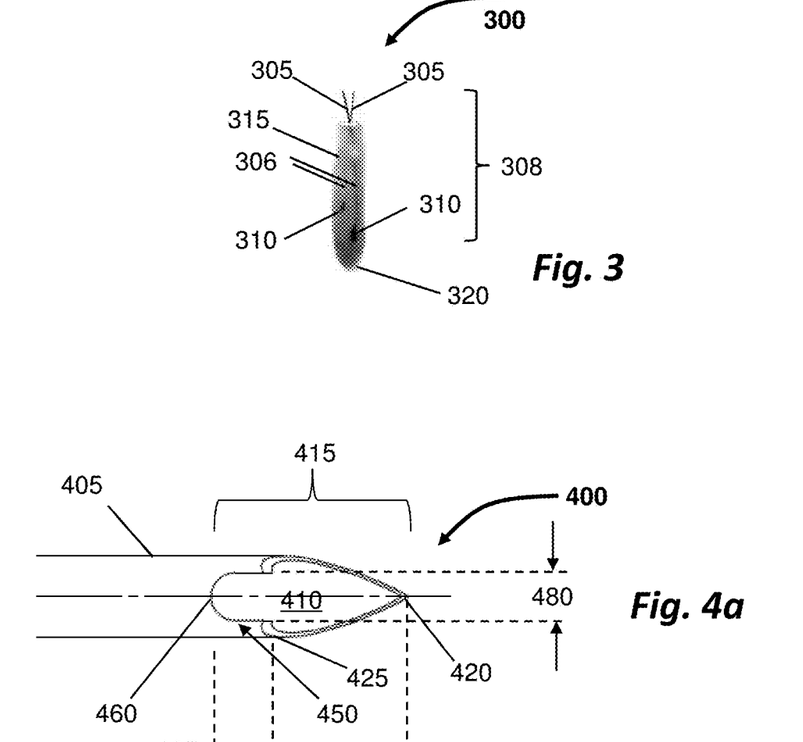
FIG. 3 illustrates a representation of the follicular unit or a hair graft.
FIGS. 4a and 4b illustrate an example of a schematic top and side view of a needle according to an embodiment of the present disclosure, respectively.

FIG. 3 depicts a follicular unit 300, comprising of one or more hair follicles or hair shafts 308, each extending from a corresponding bulb 310, the follicular unit 300 having a distal end 320 positioned beneath the skin. Typically, the hair bulb 310 and a portion 306 of the hair shaft 308 are surrounded by tissue 315 wherein a tip portion 305 of the hair shaft 308 being free of any tissue and representing a portion of the hair follicle or hair shaft that emerges from the body surface. This tip portion 305 is usually trimmed to about 1 mm to 2 mm (0.04 to 0.08 inches) when hair transplantation is performed using hand-held instruments or during an automated (e.g., robotic) follicular unit extraction procedures, and it is typically trimmed to about 3 mm to 5 mm (0.12 to 0.20 inches) when a strip hair transplantation procedure is performed. Typically for Caucasian hair, the portion of the hair graft surrounded by tissue 315 is in the region of 4-5 mm in length, and a typical follicular unit or hair graft 300 (from the distal tip 320 to the top of hair shafts 305) may be about 5 mm to 7 mm in length. For persons of other races, such as Asian or Afro-Caribbean, for example, these dimensions may differ. The stem cells responsible for the growth of hair are typically located along the portion 306 of the hair follicle 308 that is below the epidermis down through the hair bulb 310. Therefore, should a follicular unit be placed within the lumen of a 19 gauge hypodermic needle, such as that illustrated in FIG. 1, and an obturator utilized to urge the follicular unit 300 out of the lumen 110 thereof, a substantial portion of the tissue 315 surrounding at least the lower portion of the follicular unit 300 would be exposed in the opening 150 of the hypodermic needle 100, and have to push against the tissue beneath the body surface as the follicular unit entered the body surface. When progressively penetrating the body surface, the lower portion of the follicular unit 300 could therefore potentially be damaged as it entered the opening 150 at the distal end 115 of a hypodermic needle 100. Since the portion 306 of the hair follicles typically contains the stem cells responsible for hair growth, damaging the follicular units in this area may potentially reduce the chances of a successful implant, and impact the survival of the hair follicle(s).

In considering a needle for use in hair implantation, it is desirable that the recipient site is subjected to minimal trauma, and that any incision made be such that scarring is minimized and healing time reduced. In addition, implantation of a follicular unit should not cause trauma to the surrounding follicles, whether they be existing follicular units or previously-implanted follicular units. Furthermore, the size of needle adopted may depend on other factors, including but not limited to, the patient, the patient's hair texture, hair density or the needle size that will create the desired natural-looking and artistically pleasing result for the patient. Finally, the depth of implantation of a follicular unit is important to the aesthetic result and is a challenge to achieve manually, particularly with the operator fatigue that results when a large number of grafts are implanted. If the graft is implanted too deep, a divot-like appearance results; if implanted too shallow, a bump results or the follicular unit may not stay in position. In order to avoid the issues presented by the use of the needles such as those described in reference to FIGS. 1 and 2, new implant needles were developed which will be described below in reference to the examples of FIGS. 4-7.

Figure 4B:
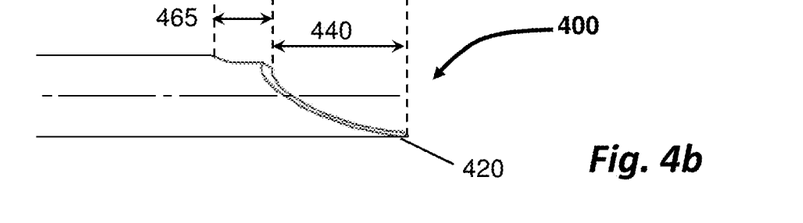

FIGS. 4a and 4b illustrate an example of the improved design of an implantation needle according to one aspect of the present disclosure. The implantation needle 400 is configured to provide a follicular unit being urged out of the distal end of the lumen with additional protection while providing a substantially non-coring incision. It has been found by applicant that improved results are achieved by configuring the implantation needle with a relief portion as described below. FIG. 4a shows the needle 400 disposed horizontally and as viewed from above. FIG. 4b is a side view of the needle of FIG. 4a. The implantation needle 400 comprises an elongated body 405 having a longitudinal axis and forming a lumen 410 therein, the lumen 410 configured to accommodate a follicular unit or hair graft. The elongated body 405 may be formed of stainless steel or other such suitable material. Those skilled in the art will be aware that other suitable materials include, but are not limited to, ceramics, composite materials, and medical grade plastics. For purposes of the description of the Figures of the present disclosure, the "distal" direction is the one towards the body surface and the "proximal" direction is away from the body surface. The elongated body comprises a wall having a thickness extending from an inner wall surface to an outer wall surface (best seen in FIG. 7a), the wall thickness typically in the range of 0.01 mm to 0.02 mm (0.004 to 0.007 inches). The distal end 415 of the implantation needle 400 comprises a slanted bevel (or beveled portion) defined by the beveled surface(s) 425 and ending in a pointed distal tip 420 for penetrating the body surface. The beveled portion extends from a distal tip 420 of the needle to a relief portion 450 that will be described in detail below. While the length of the beveled portion will slightly differ depending on whether it is measured on an outer surface of the wall of the needle or on an inner surface that forms a portion of the opening to the lumen 410, in the example of FIG. 4a, the length of the bevel 440 is shown as the length from the distal tip 420 to the end of the inner wall of the surface 425. This length 440 may be in the range of 2.5 mm to 4.0 mm (0.10 to 0.16 inches), and preferably between 2.5 mm and 3 mm for needle of various gauges. Alternatively, the length of the beveled portion may be defined relative to the outside diameter of the needle 400. For example, it may be 2.5 to 3.5 times of the outside diameter of the implantation needle 400. In some embodiments, for example, with reference to hair grafts, the length of the beveled portion may be 1 mm to 2.5 mm (for example, 2 mm) shorter than the typical length of a portion of the hair graft covered with tissue.

The relief portion 450 may comprise a narrow opening or cut-out in the wall on one side of the elongated body 405 with a distal end of the relief portion adjacent the proximal end of the beveled portion and the opposite proximal end of the relief portion terminating with a curved (e.g., semi-circular) edge 460. It will be appreciated that though illustrated as semi-circular, in other embodiments, the edge 460 may have various shapes, for example, it may be straight or deviate from being straight with some or all of its length defining a very gradual curve, though a semi-circular edge may be easier to manufacture, and may present a more non-traumatic edge to a follicular unit. The narrow opening or cut-out of the relief portion, as shown, is substantially parallel to the longitudinal axis of the needle. As illustrated, for example, for a 19 gauge needle the shape of the edge 460 may be semi-circular, and may have a radius of curvature of, for example, 0.55 mm (0.022 inches). The edge 460 of the relief portion 450 may comprise a cutting or a non-cutting edge, though a non-cutting edge is preferred. In combination, the length 465 of the relief portion 450 and the bevel length 440 in some embodiments may be up to 5 mm, however, desirably it may be less than 4.5 mm, for example, about 2.5 to 4 mm, and even more desirably, approximately 3.0 to 3.5 mm, for example, for the needles of 18-21 gauge. Described in a different manner, it is preferred that the combined length of the beveled and the relief portions be equal or less than the depth of the incision made by the implantation needle 400 in the body surface and less than the length of the hair graft (or other appropriate object) to be implanted. For example, it may be 1.0 mm to 2.5 mm shorter than the length of the hair graft. As shown in FIGS. 4*a* and 4*b*, the heel 235 of FIG. 2 is replaced according to the present disclosure with a non-cutting feature, the relief portion 450, which allows the skin to stretch and tear as with conventional hypodermic needles which have a longer bevel length, thus resulting in a semicircular or non-coring cut, while at the same time protecting the follicular unit to be implanted. Once the distal end 415 of the implantation needle 400 penetrates the body surface to a depth of, for example, 4-5 mm, the follicular unit is urged out of the distal end of the lumen 410 thereof, into the tissue, with substantially all of the tissue 315 surrounding the follicular unit disposed beneath the body surface, such that substantially no tissue 315 creeps out of the relief portion 450 above the body surface.

The relief portion 450 has a length 465 and a width 480. It was discovered that the width 480 of the relief portion 450 controls to some extent the shape of the resulting incision or cut after the distal end of the needle has penetrated the body surface and whether the tissue coring occurs. Depending on the gauge of the needle, the width 480 may be in a range of up to 90% of the outside diameter of the needle, for example, it may be in a range of 50% to 80% of the outside diameter of the needle. For example, the 18-gauge needle typically has an outside diameter of 0.05 inches, and for such needle, the width 480 may be, for example, about 0.032 inches. In another example, a smaller 20 gauge needle that has an outside diameter of 0.035 inches, may have the width 480 of the opening or cut-out of the relief portion of 0.022 inches. A width 480, such as 0.022 inches or 50% of the outside diameter of the needle, creates a desired more semi-circular or non-coring cut. A minimum length of the relief portion may depend on the length of the beveled portion and the depth the needle is inserted into the skin to make a non-coring incision. In some embodiments, it is preferred that the length 465 of the relief portion 450 is in the range of 1.0 mm to 1.5 mm (0.04 to 0.06 inches) for the needles of 18, 19 or 20 gauge. Also, generally, as previously stated, the length 465 of the relief portion may be in a range of 40% to 100% relative to the length 440 of the beveled portion.

The creation of such a combination of bevel length 440 and the length 465 of the relief portion 450 can be manufactured in a variety of ways known to those skilled in the art, and typically the order in which the steps are carried out may be varied as desired, though certain orders may contribute to greater manufacturing ease and/or efficiency. However, in one embodiment the bevel length may be formed by grinding the surfaces to create cutting edges and to form a distal tip 420, and the narrow feature forming the relief portion 450 may be formed by milling a channel or slot from the proximal end of the bevel surfaces 425 for a length 465. An additional feature provided by the relief portion 450, is that it aids in the placement and retention of the implanted follicular unit while the needle is being extracted from the body surface. Not only does the relief portion 450 provide a smaller opening and a shorter bevel length than found in conventional hypodermic needles (refer to FIG. 1), but as the entire opening is beneath the body surface during the implantation procedure, retention of the follicular unit beneath the body surface is maximized. Additionally, the length 465 of the relief portion 450 is sufficient to facilitate a significant enough portion of a follicular unit disposed at the distal end 415 of the lumen 410 to encounter tissue of the incision, when being implanted into the body surface. The encounter aiding the follicular unit to adhere to the tissue it comes into contact with, and preferably be retained therein once the implantation needle has been withdrawn from the body surface.

According to another aspect, various needle configurations of the present disclosure provide another benefit by reducing or eliminating "popping." While a recipient site implantation is in progress, a problem may occur that is referred to as "popping" or dislodging of previously implanted follicular units that are adjacent or close to the new implantation site. This is due to the downward pressure on the body surface by the implantation needle, which causes adjacent previously-implanted follicular units to be expelled or at least partially expelled. Compression of the tissue adjacent the implantation location propagates through the tissue and may extrude or expel the follicular units that are located close by. Even if the previously implanted follicular units are not completely expelled, they may be urged closer to the skin or body surface, thus compromising their successful transplant. Various examples of the embodiments of the needles described below comprise configurations and features that reduce or eliminate popping.

Figures 5, 6:
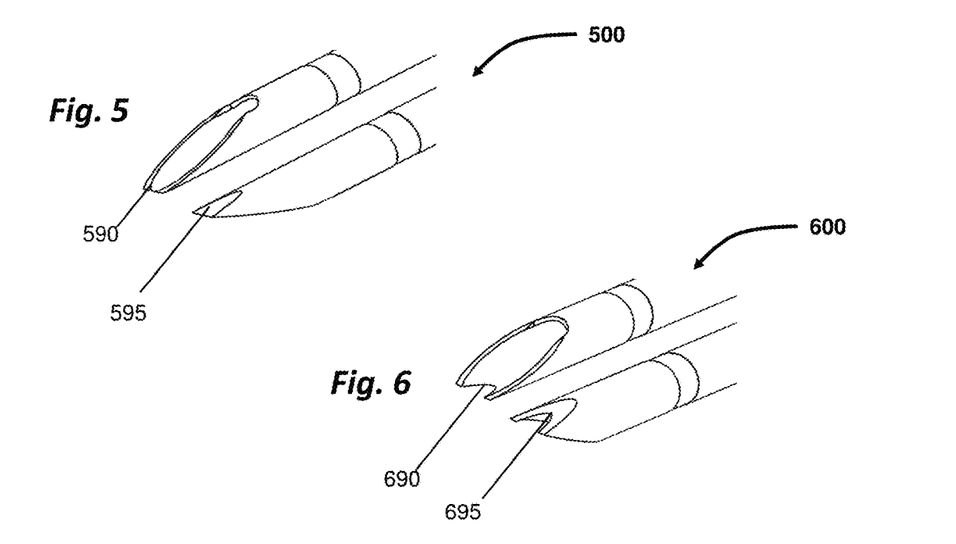
FIG. 5 is an example of a schematic perspective top and bottom view of a needle according to another embodiment of the present disclosure.
FIG. 6 is another example of a schematic perspective top and bottom view of a needle according to a further embodiment of the disclosure.

FIG. 5 illustrates an example of a needle according to another embodiment of the present disclosure. The needle in the lower figure is shown rotated 180 degrees with respect to the needle in the upper figure to provide a top and a bottom view of the configuration of the distal end of the needle of FIG. 5. The implantation needle 500 may comprise various elements of the implantation needle 400, however, it may comprise a blade-style cutting edge 590 at a distal tip instead of a sharp pointed distal tip. Creation of such an edge 590 may be formed by cutting the distal tip of the implantation needle, such as that shown in FIG. 4, off, or by grinding the tip. In one configuration, the blade-style cutting edge is formed by grinding the distal tip of the needle from the outer wall surface of the elongated body towards the inner wall surface of the elongated body to create an inclined plane 595, as illustrated more clearly in the bottom representation of the distal end of the needle in FIG. 5. This particular configuration allows for the pressure to be spread over a longer area of a blade-type cutting edge 590 rather than in a design with a pointed distal tip. Moreover, it reduces the insertion forces that are required to create an incision in the body surface, thereby reducing popping. Therefore, the blade-style edge also provides an anti-popping feature of the implantation needle 500.

Additionally, the reduction of insertion forces reduces the velocity required to insert the needle into a body surface. For example, a needle according to the embodiments of the present disclosure may reduce the velocity typically required to create an incision of a nominal 5 mm depth from 1.0 m/s to 0.3 m/s. Reduction of velocity is particularly beneficial in arrangements where multiple follicular units are temporarily stored in cartridges for subsequent implantation into a body surface. Examples of such cartridges are disclosed in the commonly assigned U.S. Pat. No. 8,211,134. In some implementations, the relatively high velocity of motion experienced by each follicular unit as it is being implanted may cause the other follicular units disposed, for example, in the nearby receptacles of the cartridge and not yet implanted, to experience some trauma or undesired motion due to this high velocity motion. Therefore, for those implementations, the reduced velocity achieved with the needle designs of the present disclosure will be beneficial.

FIG. 6 illustrates yet another example of an embodiment of a needle according the present disclosure. Similar to FIG. 5, the needle in the lower (bottom) needle representation of FIG. 6 is rotated 180 degrees with respect to the needle in the upper representation. The implantation needle 600 may comprise all or many of the elements of the implantation needle 500, except that instead of the linear blade-style cutting edge 590, it comprises a curved recessed cutting edge 690. The inclined surface 695 may be created in a manner similar to the inclined surface 595 described in reference to FIG. 5. The curved edge 690 may be formed by grinding the distal tip of the needle to create a curved recess.

FIGS. 7a-7d illustrate an embodiment of an implantation needle according to another aspect of the present disclosure with features and configurations which further reduce insertion cutting forces, allowing the implantation needle to be more easily inserted into the skin, and simultaneously reducing the pressure exerted on the surrounding body surface or scalp, thereby reducing popping.

Figures 7A, 7B, 7C, 7D:
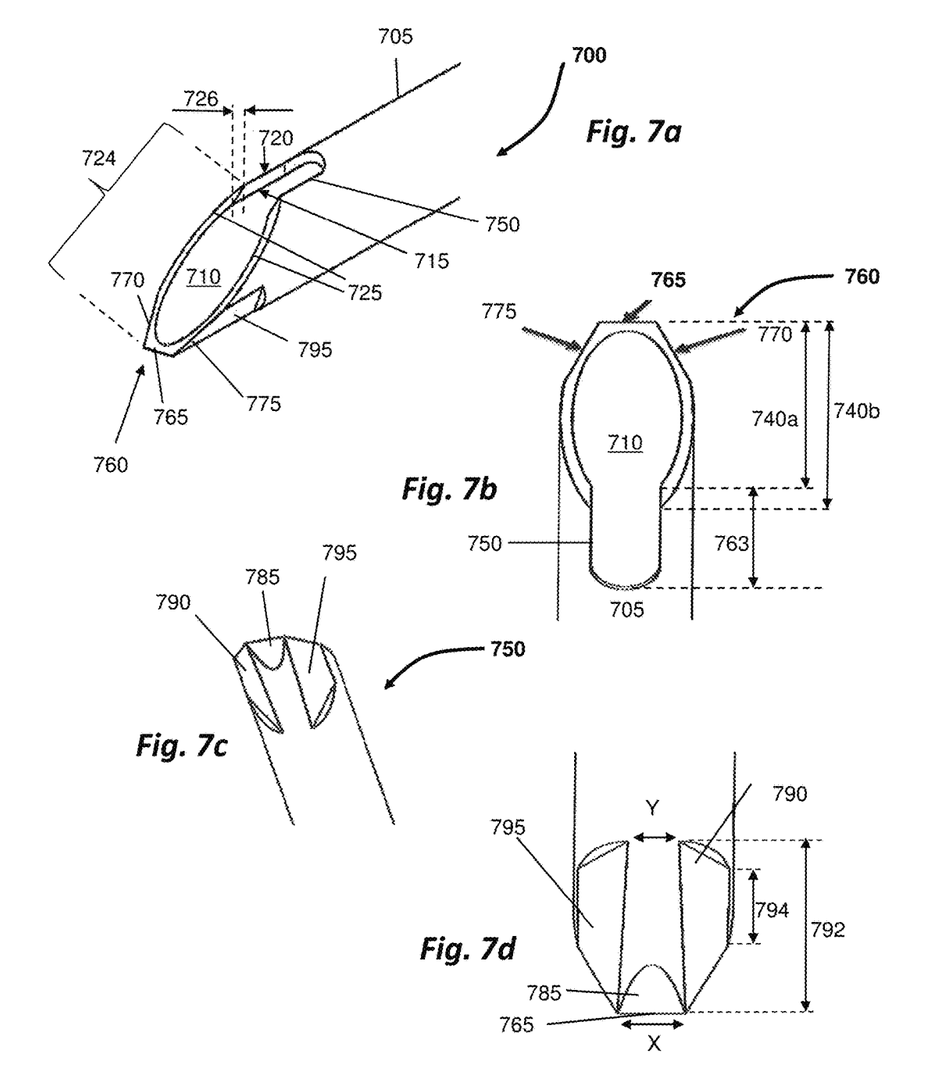
FIGS. 7a-7d show various views of an example of yet another embodiment of the present disclosure.

FIG. 7a illustrates in a perspective view a distal end of an example of the implantation needle 700. The needle 700 may comprise various elements discussed in relation to FIGS. 4 and 5 above. For example, it may have a relief portion 750 having a narrow opening or cut-out through the wall of the elongated body 705 on one (e.g., first) side of the elongated body and substantially parallel to the longitudinal axis. It may also have a beveled portion 724 oblique to the longitudinal axis with the beveled surfaces 725, the beveled portion extending from the relief portion 750 towards a distal blade-style cutting edge 760 of the needle. In some embodiments, the beveled surface 725 may comprise a plurality of connected beveled surfaces, for example, angled relative to each other, which together may form a beveled portion 724. To accomplish the goal of protecting the follicular unit while it is urged into the body surface or scalp by an obturator or other such urging device, the bevel length along a longitudinal axis of the needle may be in the region of about 2-3 mm in length. As explained in reference to FIG. 4a, the length of the beveled portion may be measured by 2 alternative measurements, as shown in reference to FIG. 7b by reference numbers 740a and 740b. If measured from the distal tip to the end of the bevel on the outside surface of the wall of the needle, then it will be slightly longer as represented by reference number 740b, and if measured from the distal tip to the end of the bevel on the inner surface of the wall that forms an opening to the lumen 710, then it will be slightly shorter as represented by reference number 740a. For example, in some embodiments, the distance 740a may be in a range of 0.07 to 0.08 inches while the distance 740b may be in a range of 0.08 to 0.09 inches. The length 763 of the relief portion (as seen in FIG. 7b) is shown measured from the proximal end of the length 740a, and in some embodiments may be in a range of 0.05 to 0.06 inches. As seen, if the length of the beveled portion is measured as shown by the reference number 740b, then there will be an overlap 726 (shown in FIG. 7a) between the length of the beveled portion and the length of the relief portion. Such overlap 726 may be, for example, about 0.011 inches.

As can be seen in FIGS. 7a-d, according to another aspect of the present disclosure, in this embodiment, the blade-style cutting edge 760 comprises three cutting segments 765, 770 and 775, though any other number of cutting segments is within the scope of this disclosure. Though illustrated as linear cutting segments, it will be appreciated that one or more of the cutting segments 765, 770, and 775 in some embodiments may comprise a non-linear or curved edge. One embodiment of the disclosure provides, for example, for the length of each segment 765, 770 and 775 to be in a range of 0.50 mm to 1.0 mm, respectively, and for the angle of the cutting segments 770 and 775 to be in the range of 100 to 120 degrees relative to a primary cutting segment 765. In the illustrated embodiment, the angles between the primary cutting segment 765 and each of the segments 770 and 775 are shown to be the same, however, in other embodiments, these angles do not have to be identical and may differ. Moreover, in the alternative embodiments, where the number of the distal blade-like cutting segments is other then 3, the angles between the adjacent segments may be in the range, for example, of about 110 to 160 degrees. The length of the most distal primary cutting segment 765 may be in a range of 20% to 30% (e.g., 25%) of the total bevel length 740a or 740b, and the length of the cutting segments 770 and 775 may be similar or different from the length of the cutting segment 765. For example, in some embodiments, the length of the cutting segments 770 and 775 may be in a range of approximately 20% to 35% of the total bevel length.

It was discovered that provision of the plurality (multiple), e.g., two or three, cutting segments having thin leading edges substantially reduces the insertion force of the needle. As stated above in reference to FIGS. 4a and 4b, the wall of the elongated body has a thickness extending from an inner wall surface 715 to an outer wall surface 720. The primary cutting segment 765 may be similar to the blade-style cutting edge 590/595 depicted in FIG. 5. This cutting segment 765 may be formed by first creating a substantially straight edge substantially perpendicular to the axis of the elongated body 705. Then the distal end of the needle may be ground from the outer wall surface 720 towards the inner wall surface 715 of the elongated body, to create an inclined plane 785. This results in a thin leading edge of the wedge-shaped primary cutting segment or blade 765. The angle of the inclined plane 785 can range from 3.0 to 7.0 degrees with respect to the outer wall surface 720 of the elongated body 705 and the length of the inclined plane 785 may be in the range of 0.015 to 0.025 inches or 0.38 to 0.63 mm. Alternatively, a grinding procedure may be utilized to create the inclined plane 785 and wedge-shaped blade 765 in one step, without first creating the substantially straight edge substantially perpendicular to the axis of the elongated body 705. Any other appropriate technique for creating the inclined plane and a thin cutting edge of the segment 765 is within the scope of the present disclosure.

The additional cutting segments 770 and 775 on either side of the primary segment 765, as shown in the example of FIGS. 7a-d, may be formed in a similar fashion by grinding the outer wall surface 720 of the elongated body 705 to create external inclined planes (or cutting surfaces) 790 and 795 respectively and resulting in the thin sharper leading cutting edges of the segments 770 and 775. It was also discovered that the two inclined planes (or cutting surfaces) 790 and 795 do not have to have their surfaces substantially parallel to the axis of the elongated body 705. The angle of the external inclined planes (or cutting surfaces) can range from 0.5 to 1.0 degrees with respect to the outer wall of the elongated body 705.

As shown more clearly in FIG. 7d, by tilting or slanting the external cutting surfaces 790 and 795 towards the inner wall surface 715 of the lumen 710, a structure may be formed in which more material has been removed from the outer wall surface 720 of the elongated body 705 in a proximal direction from the distal tip of the implantation needle. In some embodiments, slanting the external cutting surfaces 790 and 795 may result in the formation of a quadrilateral shaped surfaces, where the length 794 of a portion (or side) of the cutting surface 790 or 795 may be about 0.03 to 0.035 inches, for example, 0.032 inch (or 0.81 mm) and the length 792 of a longer portion (or side) of the cutting surface 790 and/or 795 may be about 0.07 to 0.075 inches, for example, 0.071 inch (or 1.803 mm). In this manner, the length X of the cutting edge of the primary segment 765 is longer than the distance Y formed by the proximal ends of the two inclined planes (cutting surfaces) 790, 795. In this manner the additional cutting segments 770 and 775 may be made sharper, allowing the needle to more easily penetrate the body surface. This also provides a means for reducing the insertion cutting force required in creating the incision. The blade-style cutting edges of this embodiment enable the needle to be easily inserted into the body surface. Moreover, reduction in cutting force allows the pressure in the surrounding area (the region around where the incision is made) to be reduced. Reduction in scalp pressure further aids in minimizing the popping of adjacent previously implanted follicular units or grafts.

Figure 8:
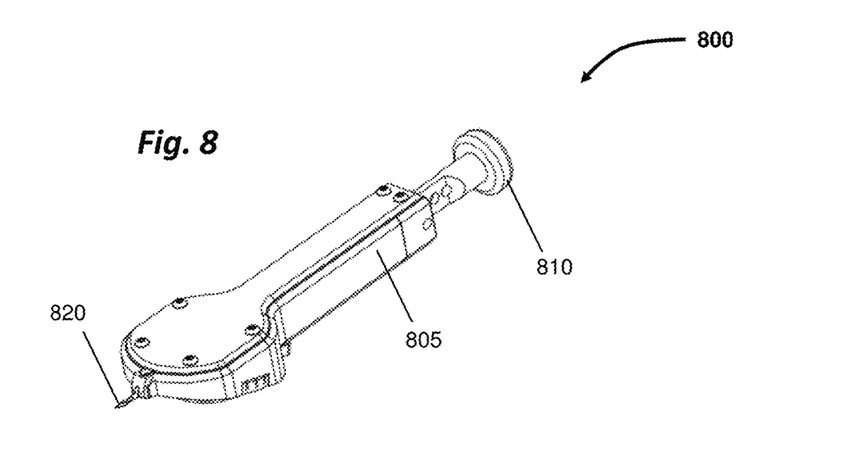
FIG. 8 is an example of a hand-held apparatus for hair implantation that can be used with needles of the present disclosure.

The implantation needles of the present disclosure may be utilized in hand-held devices and instruments or those attached, for example, to the robotic art; they can also be used in conjunction with manual devices, semi-automated, or fully automated systems. FIG. 8 illustrates an example of a hand-held instrument 800 for implanting hair grafts into a body surface that may utilize the implantation needles of the present disclosure. In a hand-held devices, hair grafts can be loaded in such device individually (not shown) or into a plurality of receptacles of a storage cartridge that may be operatively attached to a body 805 of such hand-held device, as seen in FIG. 8. In use, the user may activate a plunger 810, which operates an urging mechanism, such as an obturator or a pressure differential (not shown) to urge a follicular unit, for example, from a chamber of the hand-held device where it is previously placed or loaded, or (in case of the use of the storage cartridge) from a receptacle of the cartridge disposed on the hand-held device, into the implantation needle 820, and eventually out of the distal end of the needle 820 into a body surface, e.g., a scalp.

Figure 9:
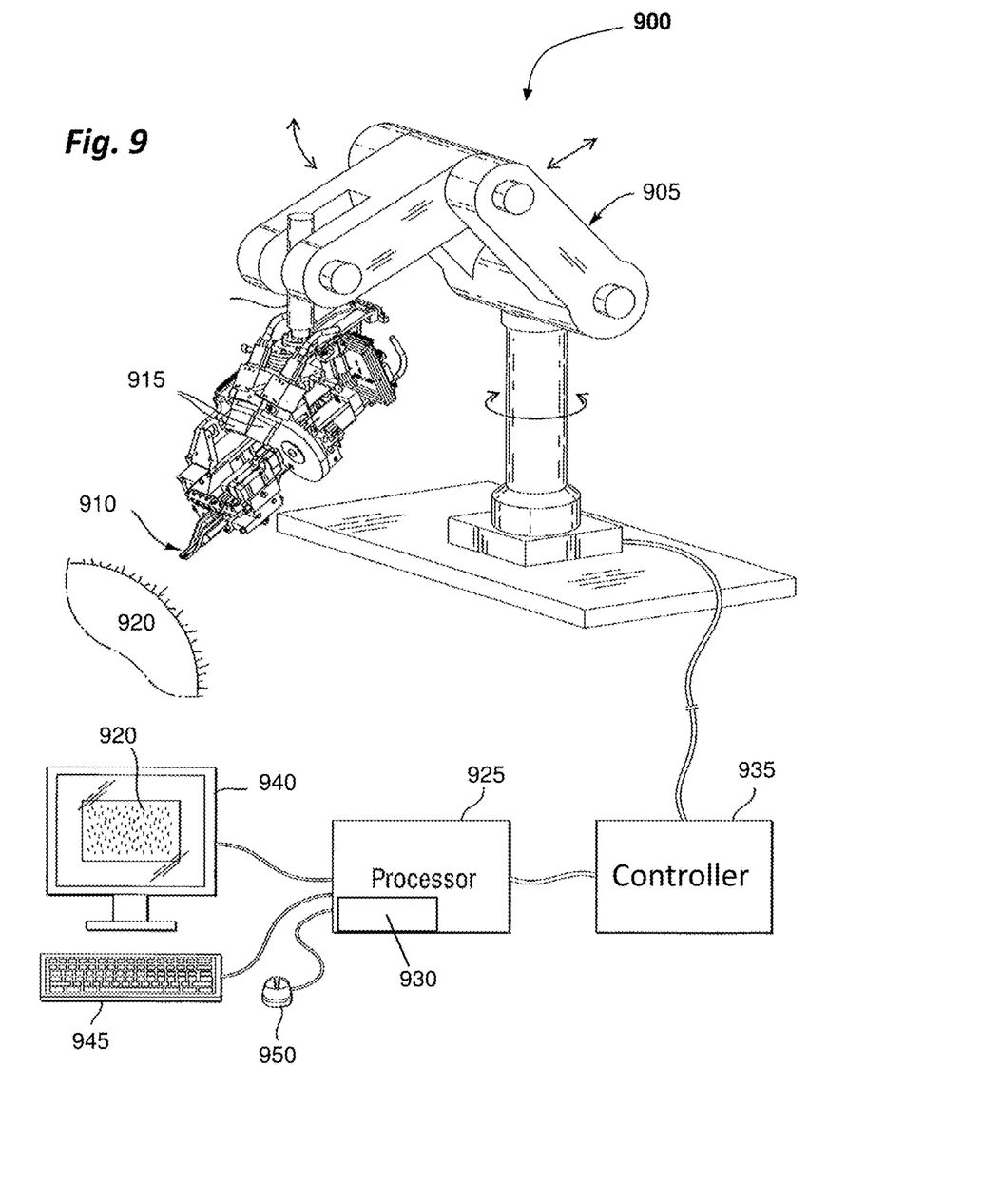
FIG. 9 is a schematic perspective view of an example of a robotic system that can be utilized with the needles of the present disclosure.

FIG. 9 is a schematic perspective view of an example of a robotic system 900 that may be used, for example, for implanting follicular units into a body surface, such as the scalp. The system 900 includes a robotic arm 905 to which is coupled a tool 910, for example an implanting tool. Various motors and other movement devices may be incorporated to enable fine movements of an operating tip of the tool 910 in multiple directions. The robotic system 900 further includes at least one or more (and preferably two for stereo vision) image acquisition device 915 which may be mounted in a fixed position, or coupled (directly or indirectly) to a robotic arm 905 or other controllable motion device. The image acquisition device 915 may comprise a device that takes still images, it can also comprise a device capable of real time imaging (e.g., webcam capable of continuously streaming real time information), and/or it could also have a video recording capability (such as a camcorder). The image acquisition device may be coupled to one or more processor or a processing system 925, which in the example of FIG. 9 incorporates an image processor 930, to control the imaging operation and process image data. The operating tip of the tool 910 is shown positioned over a body surface 920, in this case a part of the patient scalp having hair follicles thereon.

Typically, the processor 925 operates as a data processing device, and may execute a program that may be configured to include predetermined operations and may be incorporated into a computer. Alternatively, the program may include a plurality of modules that perform such sub-operations of an operation, or may be part of a single module of a larger program providing the operation. The modular construction facilitates adding, deleting, updating and/or amending the modules therein and/or features within the modules. The processor may access the memory in which may be stored at least one sequence of code instructions comprising the program for performing predetermined operations. The memory and the program may be located within the computer or may be located external thereto. The processor 925 may include a central processing unit or parallel processor, and input/output interface, a memory with a program, wherein all the components may be connected by a bus. These components are generally known in the art and, therefore, they do not need to be described in detail here.

The processor 925 may comprise an image processor 930 for processing images obtained from the image acquisition device 915. The image processor 930 may be a separate device or it may be incorporated as a part of the processor 925. By way of example, and not limitation, a suitable image processor 930 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). The processor/image processor may also include memory, storage devices, and other components generally known in the art and, therefore, they do not need to be described in detail here.

The processor 925 may also instruct the various movement devices of the robotic arm 905, including the tool 910, and act, for example, through a controller 935 as schematically shown in FIG. 9. The controller 935 may be operatively coupled to the robotic arm and configured to control the motion of the robotic arm, including the motion based on the images or data acquired by the image acquisition device. Alternatively, controller 935 may be incorporated as a part of the processor 925, so that all processing and controls of all movements of all the tools, the robotic arm and any other moveable parts of the assembly, including those based on the images or data acquired by the image acquisition device, are concentrated in one place. The system 900 may further comprise other tools, devices and components useful in harvesting, and/or implantation of the hair follicles, or in hair transplantation planning.

The system further comprises an interface adapted to receive an image data, various parts of the system allowing an operator to monitor conditions and provide instructions, as needed. A user interface may comprise elements such as a display device 940, and user input devices such as a keyboard 945 and mouse 950. The interface may also include hardware ports, cables, leads, and other data transmission means, or it may comprise a computer program. The processor 925 may interact with the imaging device 915 via the interface. It will be apparent that the user input device may optionally comprise a track pad, track ball, stylus, pen or line tool, a touch-enabled device, tablet or other such similar device on which one may use one's fingers or gestures, to input commands. A magnified image of the body surface 920 can be seen on the display device, screen or monitor 940. In addition, the system 900 may comprise other tools, devices and components useful in harvesting, and/or implantation of the hair follicles, or in hair treatment planning.

The various embodiments described above are provided by way of illustration only and should not be construed to limit the claimed disclosure. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields, for example, those where reduction of the insertion force or a non-coring qualities are desired. The description, therefore, is not to be taken in a limiting sense, and the scope of the present disclosure is defined by the appended claims. It will be further appreciated by those skilled in the art that the application is not limited to the use of a particular system, and that automated (including robotic), semi-automated, and manual systems and apparatus may be used for positioning and actuating various implantation needles and components disclosed herein.

What is claimed is:

1. A hair implantation needle comprising:
   an elongated body having a longitudinal axis and a lumen sized to receive a follicular unit; and
   a distal end with a distal tip configured to penetrate a body surface;
   wherein the distal end comprises:
      a beveled portion extending from the distal tip oblique to the longitudinal axis of the elongated body; and
      a relief portion extending from the beveled portion in a proximal direction, the relief portion comprising a narrow cut-out in a wall of the elongated body substantially parallel to the longitudinal axis,
      wherein the beveled portion and the relief portion are configured and sized relative to each other to prevent coring and provide a non-coring needle,
      wherein the beveled portion and the relief portion together form an oblique opening at the distal end having a length of less than 4 mm.

2. The implantation needle of claim 1, wherein the beveled portion and the relief portion together form an oblique opening at the distal end having a length approximately equal to or less than a depth of an incision to be formed by the implantation needle.

3. The implantation needle of claim 1, wherein a length of the relief portion is between 40% and 100% percent of a length of the beveled portion.

4. The implantation needle of claim 1, wherein the relief portion comprises a width, the width of the relief portion being less than 90% of an outside diameter of the lumen.

5. The implantation needle of claim 1, wherein the relief portion comprises a proximal edge having a non-cutting edge.

6. The implantation needle of claim 1, wherein a length of the beveled portion is about 2.5 times to 3.5 times of an outside diameter of the needle.

7. The implantation needle of claim 1, wherein the beveled portion comprises beveled surfaces comprising a plurality of connected beveled surfaces angled relative to each other.

8. The implantation needle of claim 1, wherein the beveled portion and the relief portion together form an oblique opening at the distal end of the needle, and the beveled portion and the relief portion may be sized relative to each other such that a length of the oblique opening is less than a length of the follicular unit to be implanted.

9. A hair implantation needle comprising:
   an elongated body having a longitudinal axis and a lumen sized to receive a follicular unit; and
   a distal end with a distal tip configured to penetrate a body surface;
   wherein the distal end is non-coring and comprises:
      a beveled portion extending from the distal tip oblique to the longitudinal axis of the elongated body; and
      a relief portion extending from the beveled portion in a proximal direction, the relief portion comprising a narrow cut-out in a wall of the elongated body substantially parallel to the longitudinal axis, wherein a length of the relief portion is approximately 40% to 100% of a length of the beveled portion,
      wherein the relief portion comprises a width of between 50 and 80% of the lumen of the elongated body.

10. The hair implantation needle of claim 9, wherein a length of the beveled portion measured along the longitudinal axis of the needle comprises a length in a range of about 2 to 3 mm.

11. The hair implantation needle of claim 9, wherein the distal tip comprises a sharp pointed end.

12. A hair implantation needle comprising:
   an elongated body having a longitudinal axis and a lumen sized to receive a follicular unit; and
   a distal end with a distal tip configured to penetrate a body surface;
   wherein the distal end comprises:
      a beveled portion extending from the distal tip oblique to the longitudinal axis of the elongated body; and
      a relief portion extending from the beveled portion in a proximal direction, the relief portion comprising a narrow cut-out in a wall of the elongated body substantially parallel to the longitudinal axis,
      wherein the beveled portion and the relief portion are configured and sized relative to each other to prevent coring and provide a non-coring needle,
      wherein the relief portion comprises a width, the width of the relief portion being less than 90% of an outside diameter of the lumen.

13. A hair implantation needle comprising:
   an elongated body having a longitudinal axis and a lumen sized to receive a follicular unit; and a distal end with a distal tip configured to penetrate a body surface;

wherein the distal end comprises:

a beveled portion extending from the distal tip oblique to the longitudinal axis of the elongated body; and a relief portion extending from the beveled portion in a proximal direction, the relief portion comprising a narrow cut-out in a wall of the elongated body substantially parallel to the longitudinal axis, wherein the beveled portion and the relief portion are configured and sized relative to each other to prevent coring and provide a non-coring needle, wherein a length of the beveled portion is about 2.5 times to 3.5 times of an outside diameter of the needle.

14. A hair implantation needle comprising:

an elongated body having a longitudinal axis and a lumen sized to receive a follicular unit; and a distal end with a distal tip configured to penetrate a body surface;

wherein the distal end is non-coring and comprises:

a beveled portion extending from the distal tip oblique to the longitudinal axis of the elongated body; and a relief portion extending from the beveled portion in a proximal direction, the relief portion comprising a narrow cut-out in a wall of the elongated body substantially parallel to the longitudinal axis, wherein a length of the relief portion is approximately 40% to 100% of a length of the beveled portion, wherein a length of the beveled portion measured along the longitudinal axis of the needle comprises a length in a range of about 2 to 3 mm.

* * * * *